United States Patent
Volker

(10) Patent No.: US 9,254,358 B2
(45) Date of Patent: Feb. 9, 2016

(54) RO SYSTEM AND METHOD FOR DISINFECTING LINES OF THE RO SYSTEM

(76) Inventor: Manfred Volker, Blankenbach (DE)

(*) Notice: Subject to any disclaimer, the term of this patent is extended or adjusted under 35 U.S.C. 154(b) by 446 days.

(21) Appl. No.: 13/602,656

(22) Filed: Sep. 4, 2012

(65) Prior Publication Data

US 2014/0027379 A1  Jan. 30, 2014

(30) Foreign Application Priority Data

Jul. 26, 2012  (EP) .................................. 12005434

(51) Int. Cl.
| | | |
|---|---|---|
| C02F 1/44 | (2006.01) | |
| B01D 65/02 | (2006.01) | |
| C02F 1/78 | (2006.01) | |
| A61M 1/16 | (2006.01) | |
| B01D 61/08 | (2006.01) | |

(Continued)

(52) U.S. Cl.
CPC ............. *A61M 1/168* (2013.01); *A61M 1/1688* (2014.02); *B01D 61/08* (2013.01); *B01D 61/10* (2013.01); *B01D 61/58* (2013.01); *B01D 65/022* (2013.01); *C02F 1/441* (2013.01); *A61M 1/16* (2013.01); *A61M 1/169* (2013.01); *A61M 1/1656* (2013.01); *B01D 61/243* (2013.01); *B01D 2311/06* (2013.01); *B01D 2311/25* (2013.01); *C02F 1/4672* (2013.01); *C02F 2103/026* (2013.01); *C02F 2209/04* (2013.01); *C02F 2209/23* (2013.01); *C02F 2307/14* (2013.01)

(58) Field of Classification Search
CPC ..... A61M 1/169; A61M 1/16; A61M 1/1688; A61M 1/168; A61M 1/1656; C02F 1/441; C02F 1/4672; C02F 2103/026; C02F 2307/14; C02F 2209/04; C02F 2209/23; B01D 61/08; B01D 61/10; B01D 61/58; B01D 61/243; B01D 65/022; B01D 2311/06; B01D 2311/25

See application file for complete search history.

(56) References Cited

U.S. PATENT DOCUMENTS

| | | | | |
|---|---|---|---|---|
| 6,908,546 | B2* | 6/2005 | Smith | ........................... 210/137 |
| 2009/0134080 | A1* | 5/2009 | Fabig | ........................... 210/137 |

FOREIGN PATENT DOCUMENTS

| | | |
|---|---|---|
| DE | 10013964 | 9/2001 |
| DE | 10262036 | 6/2004 |

(Continued)

OTHER PUBLICATIONS

Machine Translation of DE 102009057562, Publication Date 2011-0-16 (Voelker) using Espacenet.*

(Continued)

*Primary Examiner* — Katherine Zalasky
*Assistant Examiner* — Benjamin Lebron
(74) *Attorney, Agent, or Firm* — Greer, Burns & Crain, Ltd

(57) ABSTRACT

A circulation pump and an electrochemical ozone generator are integrated into the permeate return line of an RO system, and the permeate return line is connected in flow direction behind the circulation pump and the ozone generator by a recirculation line to the permeate supply line, which can form a closed circuit where the ozonized permeate circulates until all organic contaminants have been killed or decomposed by the ozone in that part of the line system. Valves are integrated, respectively, into the recirculation line and the permeate return line downstream of the branch of the recirculation line. During normal operation of the RO system, the recirculation line valve is connected for feeding connected dialysis devices while the permeate return line valve is open, so excessive permeate that was not taken by the dialysis devices can flow into the supply tank. Alternatively, the permeate can be discharged into an outlet.

9 Claims, 1 Drawing Sheet

(51) Int. Cl.
  *B01D 61/10* (2006.01)
  *B01D 61/58* (2006.01)
  *C02F 1/467* (2006.01)
  *C02F 103/02* (2006.01)
  *B01D 61/24* (2006.01)

(56) References Cited

FOREIGN PATENT DOCUMENTS

| DE | 10319221 | 7/2004 | | |
|---|---|---|---|---|
| DE | 102009057562 | 6/2011 | | |
| DE | 2010006823 | 9/2011 | | |
| EP | 1902771 A2 * | 3/2008 | ............ | B01D 61/025 |

OTHER PUBLICATIONS

Human Translation of DE 10319221, Publication Date Jul. 29, 2004 (Heller).*
European Patent Organization, European Search Report, European Application 12 00 5434, Jan. 4, 2013.
European Patent Organization, Written Opinion of the Search Authority, European Application 12 00 5434, Jan. 18, 2013.

* cited by examiner

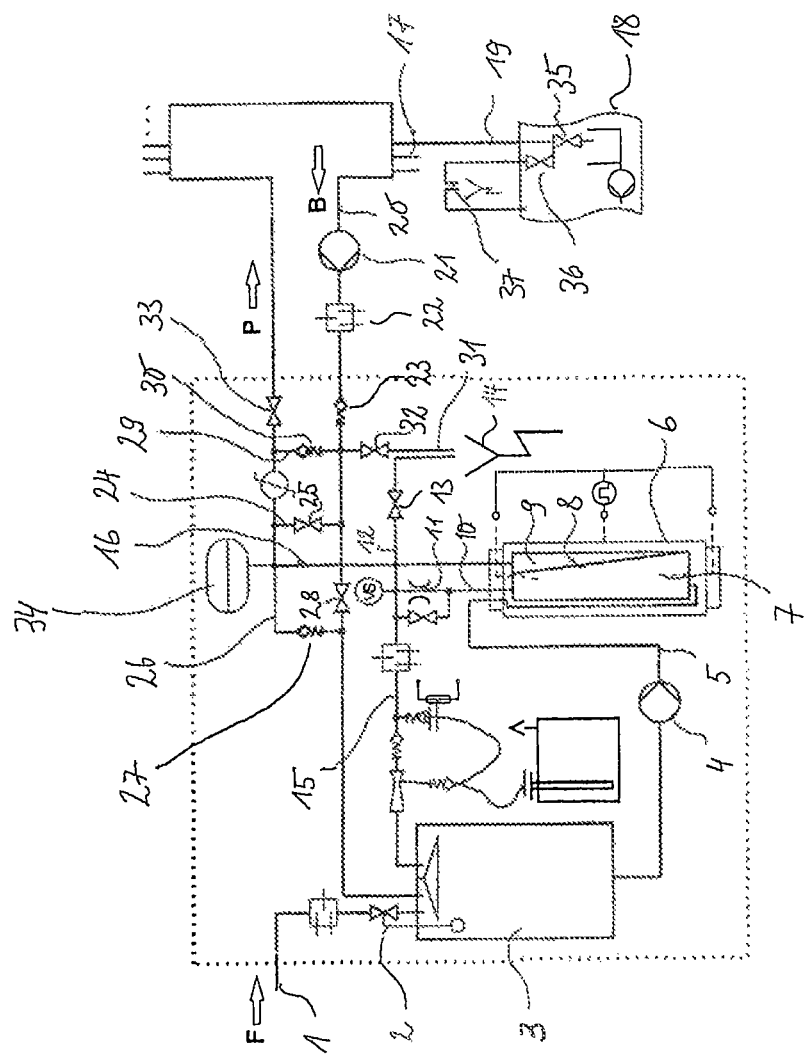

RO SYSTEM AND METHOD FOR DISINFECTING LINES OF THE RO SYSTEM

FIELD OF THE INVENTION

The present invention refers to an RO system with which ultrapure water is preferably produced for the operation of dialysis devices. The RO system comprises an RO filter module which is subdivided by a membrane into a primary chamber and a secondary chamber, an atmospherically ventilated supply tank in which a raw-water supply line terminates, a line which leads from the lower end of the supply tank to the primary chamber and into which a pump is integrated, a concentrate line which leads away from the primary chamber and preferably leads back to the supply tank, and a permeate supply line which extends from the secondary chamber of the filter module and to which at least one dialysis device is connectable by means of a branch line or secondary ring line, wherein further, in flow direction behind the connection of the at least one dialysis device, an adjacent permeate return line leads back to the supply tank.

BACKGROUND

The line system of an RO system must be decontaminated from time to time because otherwise organic deposits may settle in the interior of the lines and associated functional units, such as valves, etc., and it may be infested by germs that might be harmful to the health of patients treated by means of the dialysis devices. So far the line system of RO systems has been disinfected in practice with chemical agents or by hot cleaning. The hot cleaning process requires a huge amount of energy, and when chemical cleaning agents are used, one must make sure by taking utmost care that after decontamination there are no chemical residues remaining in the line system and its functional units.

SUMMARY OF THE INVENTION

It is the object of the present invention to indicate an RO system of the kind in question that permits a gentle decontamination at least of the area of the permeate line, while ensuring at the same time that no pump gets damaged due to the cleaning operation.

This object is achieved with an RO system and method, advantageous features and developments of which are more fully described herein below.

According to the invention a circulation pump and an electrochemical ozone generator are integrated into the permeate return line of the RO system, and the permeate return line is connected in flow direction behind the circulation pump and the ozone generator by a recirculation line to the permeate supply line, whereby a closed circuit can be formed in which ozonized permeate can circulate until all organic contaminants in that part of the line system have been killed off or decomposed by the ozone. A respective valve is integrated into the recirculation line and into the permeate return line downstream of the branch of the recirculation line. The valve of the recirculation line is closed during normal operation of the RO system for feeding connected dialysis devices, while the valve in the permeate return line is open, so that excessive permeate that was not taken by the dialysis devices can flow back into the supply tank. Alternatively, the permeate can also be discharged into an outlet.

By contrast, when the valve in the permeate return line is closed and the valve in the recirculation line is opened, the system is in the cleaning state in which the ozone generator enriches the permeate flowing therethrough with ozone.

Moreover, according to the invention a permeate return-line section which terminates in the permeate return line downstream of the valve arranged therein branches off from the permeate supply line upstream of the termination of the recirculation line into the permeate supply line, and a pressure holding valve is arranged in the permeate return-line section. This has the effect that the RO system can continue its operation also in the disinfection mode and uninterruptedly produces permeate that can flow off through the permeate return-line section into the supply tank of the RO system. When no additional permeate is needed in the recirculation circuit of the ozonized permeate, the whole amount of the fresh permeate produced during recirculation flows off through the pressure holding valve to the supply tank in that in the return line section before the valve such a pressure is built up that it exceeds the closing force of the valve. Instead of such a pressure holding valve, a valve may also be provided that is e.g. electrically controlled by a control device of the RO system.

The ozonized permeate circulating in the permeate recirculation circuit can however also be used for cleaning the line system leading to the water inlet valve of a dialysis device, with ozonized permeate being discharged through the associated discharge line into an outlet in the opened condition of the flushing valve. This can take place consecutively in all connected dialysis devices.

In this case fresh permeate, i.e. permeate that has not been ozonized yet, flows into the recirculation circuit because, otherwise, the circuit might more or less run empty, whereby the operativeness of the pump arranged in the recirculation circuit might get impaired. Here, either the whole amount of the supplied fresh permeate flows temporarily into the recirculation circuit or, however, the needed partial amount, whereas the other partial amount flows off through the permeate return-line section to the supply tank.

In further details, it is provided that a further valve is integrated downstream after the termination of the recirculation line into the permeate supply line, and that upstream of the further valve a connection line branches off to the permeate return line, into which a further pressure holding valve is integrated. Advantageously, an outflow line which leads to an outlet and into which an outflow valve is integrated branches off at the termination of the connection line into the permeate return line or between said termination and the valve integrated into the permeate return line.

Hence, the method according to the invention for disinfecting the permeate line system provides that during a cleaning process the permeate is provided with ozone while observing a predetermined ozone concentration, and the ozonized permeate circulates in the permeate line while at least a partial stream of the permeate arriving from the secondary chamber of the filter module can flow to the supply tank without mixing with the ozone-enriched permeate. After a predetermined cleaning time the ozonized permeate is flushed into an outlet or is fed to the supply tank of the RO system. In the last-mentioned case the ozonized permeate which is fed to the supply tank can also disinfect the supply tank itself and optionally also the line leading to the filter module. Since the membrane of the filter may get damaged by ozone, starting from a specific concentration, it is also possible with a small amount of ozone in the liquid to clean the primary chamber of the filter module and the concentrate return line, which preferably leads back to the supply tank. To this end the ozone concentration is monitored at suitable places of the line system. For this purpose at least one measuring chamber is arranged in the line system for controlling the amount of ozone in the liquid by means of redox potential or ozone sensors.

According to a further proposal of the invention the amount of the ozone produced by the ozone generator can be controlled and monitored by a selected applied voltage and/or a selected current.

The recirculation circuit of the permeate line system with the aforementioned valves and the recirculation pump according to the invention can also be used for cleaning or disinfecting this area of the RO system with the help of a chemical disinfectant or also with a thermal device instead of the ozone generator. In this case the RO system can also continue its operation during the cleaning process and supply permeate, whereby idling of the circulation pump is prevented, and the feed lines of the connected dialysis devices have to be cleaned or disinfected.

Further details of the invention become apparent from the subsequent description and from the drawing.

BRIEF DESCRIPTION OF THE DRAWINGS

FIG. 1 is a schematic illustration of the line system of an embodiment of the RO system according to the invention with the associated functional units.

DETAILED DESCRIPTION

Described are only the components of the FIGURE that are of importance to the present invention.

Liquid is supplied through a line 1 to the RO system, the liquid passing via an inlet valve 2 into the supply tank 3. The liquid in the supply tank 3 is supplied by means of a pump 4 through a line 5 to an RO filter module 6, the primary chamber 7 of which is separated by a membrane 8 from the secondary chamber 9.

Concentrate is discharged from the primary chamber 7 through a line 10 in which a throttle 11 provides the pressure prevailing in the primary chamber 7. The concentrate can either be discharged through a line 12, into which a valve 13 is integrated, into an outlet 14 or can be returned through a concentrate return line 15 into the supply tank 3.

Permeate flows out of the secondary chamber 9 through a permeate supply line 16 to connections 17 of dialysis devices that in an illustrated example can be supplied with permeate through a respective branch line 19. The dialysis devices can also be fed with the help of secondary lines, which are here not shown. Downstream of the last connection of a dialysis device, the permeate supply line 16 is followed by a permeate return line 20 which leads back to the supply tank 3.

A circulation pump 21 and an ozone generator 22 are integrated into the permeate return line 20 in flow direction one after the other, the ozone generator 22 being followed by a pressure holding valve 23. Another position of the circulation pump and the ozone cell e.g. in the permeate supply line or the use of a thermal or chemical disinfecting/cleaning device is also within the scope of the invention.

A recirculation line 24 with a valve 25 arranged therein connects the permeate return line 20 to the permeate supply line 16, whereby a recirculation circuit is formed in which ozonized permeate can circulate.

In flow direction before the recirculation line 24 a permeate return-line section 26 branches off from the permeate supply line 16 and has integrated therein a pressure holding valve 27 which during disinfection or cleaning defines the ring prepressure and through which excessive permeate flows off.

The permeate return-line section 26 terminates in the permeate return line 20 downstream of a valve 28 integrated thereinto.

Downstream of the termination of the recirculation line 24 into the permeate supply line 16, a connection line 29 with a pressure holding valve 30 branches off and terminates in the permeate return line 20 and leads from there as an outflow line 31 with a shut-off valve 32 to the outlet 14. Downstream of the connection line 29, the permeate supply line 16 has disposed therein a further valve 33 which can be controlled by the conductivity temperature measurement 34.

The branch line 19 leads to a water inlet valve 35 of a dialysis device 18. An outflow line 37 which leads to an outlet and has a flushing valve 36 is branched off directly before the water inlet valve 35.

| Legend | Designation |
| --- | --- |
| 1 | Liquid supply |
| 2 | Inlet valve |
| 3 | Supply tank |
| 4 | Pump |
| 5 | Feed line filter module |
| 6 | Filter module |
| 7 | Primary chamber |
| 8 | Membrane |
| 9 | Secondary chamber |
| 10 | Concentrate line |
| 11 | Throttle |
| 12 | Line |
| 13 | Concentrate outflow valve |
| 14 | Outlet |
| 15 | Concentrate return line |
| 16 | Permeate supply line |
| 17 | Connections dialysis device |
| 18 | Dialysis device |
| 19 | Branch line |
| 20 | Permeate return line |
| 21 | Circulation pump |
| 22 | Electrochemical ozone generator |
| 23 | Pressure holding valve |
| 24 | Recirculation line |
| 25 | Recirculation valve |
| 26 | Part permeate return |
| 27 | Pressure holding valve |
| 28 | Return shut-off valve |
| 29 | Connection line |
| 30 | Pressure holding valve |
| 31 | Outflow line |
| 32 | Ring outflow valve |
| 33 | Ring-pressure protection valve |
| 34 | Temperature conductivity monitoring |
| 35 | Water inlet valve dialysis device |
| 36 | Dialysis-device flushing valve |
| 37 | Outflow line |

The invention claimed is:

1. A reverse osmosis (RO) system comprising an RO filter module which is subdivided by a membrane into a primary chamber and a secondary chamber, comprising a raw-water supply line leading to a ventilated supply tank, a line with an integrated pump leading from the ventilated supply tank to the primary chamber, a concentrate line leading away from the primary chamber, and a permeate supply line leading from the secondary chamber, with at least one dialysis device being connectable to the permeate supply line by way of a branch line or secondary ring line, and an adjacent permeate return line downstream of the at least one dialysis device leading back to the ventilated supply tank, wherein a circulation pump and an electrochemical ozone generator are integrated into the permeate return line, wherein a recirculation line connects the permeate return line downstream of the circulation pump and the ozone generator to the permeate supply line, with a recirculation valve integrated into the recirculation line and a return shutoff valve integrated into the permeate return line at a location downstream of the recirculation line, and wherein a permeate return-line section, terminating at one end in the permeate return line downstream of the valve arranged therein, and at an opposite end in the permeate supply line, the opposite end of the permeate return-line section branching off from the permeate supply line upstream of the termination of the recirculation line into the permeate supply line, and wherein a pressure holding valve is arranged in the permeate return-line section, so that the RO system can continue to operate even during a disinfecting mode and produces permeate without interruption and either an entire permeate volume or a proportion of the permeate flows back to the ventilated supply tank.

2. The RO system according to claim 1, wherein
a further valve is integrated into the permeate supply line downstream of the recirculation line to the permeate supply line.

3. The RO system according to claim 2, wherein
between the termination of the recirculation line into the permeate supply line and the further valve a connection line branches off to the permeate return line into which a further pressure holding valve is integrated.

4. The RO system according to claim 1, wherein
an outflow line, which leads to an outlet and into which an outflow valve is integrated, branches off at an intersection of the connection line and the permeate return line or branches off between said outflow line and the valve thereof.

5. The RO system according to claim 1, wherein
the amount of the ozone produced by the ozone generator is controllable by a selected applied voltage and/or a selected current.

6. The RO system according to claim 1, wherein
a measuring chamber is positioned in the permeate supply line or the permeate return line for monitoring the ozone concentration and for controlling the ozone amount in the liquid by way of redox potential or ozone sensors.

7. A method for disinfecting lines of a reverse osmosis (RO) system, comprising the steps of:
providing, during a cleaning process of the RO system, permeate with ozone while observing a predetermined ozone concentration and circulating ozonized permeate in a permeate supply line, permeate return line, and recirculation line, while the RO system continues to operate and produces permeate without interruption and either an entire volume or at least a proportion of the permeate coming from a secondary chamber of a filter module flows to a supply tank without mixing with ozone-enriched permeate, flushing, after a predetermined time, the ozonized permeate into an outlet or to the supply tank of the RO system, effectively preventing the ozone-enriched permeate from entering the supply tank by providing a pressure holding valve in a permeate return-line section that extends between the permeate supply line and the permeate return line, the permeate return line extending to the supply tank, and by providing a return shutoff valve in the permeate return line downstream of the recirculation line.

8. The method according to claim 7, wherein
the ozonized permeate fed to the supply tank disinfects the supply tank and preferably the line leading to the filter module, the primary chamber of the filter module, and the concentrate return line.

9. The method according to claim 7, wherein
the ozonized permeate flows to a closed water inlet valve of a dialysis device and discharges through an associated outflow line with an open flushing valve, while a partial stream of permeate exits out of the secondary chamber and flows into the permeate supply line.

* * * * *